United States Patent

Breuer

[11] 3,960,849
[45] June 1, 1976

[54] AMINO-1,2,4-OXADIAZOLYL-3-ACETYL CEPHALOSPORINS

[75] Inventor: Hermann Breuer, Regensburg, Germany

[73] Assignee: E. R. Squibb & Sons, Inc., Princeton, N.J.

[22] Filed: Mar. 13, 1974

[21] Appl. No.: 450,928

[52] U.S. Cl............................. 260/243 C; 424/246; 260/239.1; 424/271
[51] Int. Cl.².............. C07D 499/44; C07D 501/20
[58] Field of Search .......................... 260/243 C

[56] References Cited
UNITED STATES PATENTS

| | | |
|---|---|---|
| 3,516,997 | 6/1970 | Takano et al................... 260/243 C |
| 3,743,644 | 7/1973 | Essery et al..................... 260/243 C |
| 3,821,207 | 6/1974 | Chow et al...................... 260/243 C |

*Primary Examiner*—Nicholas S. Rizzo
*Attorney, Agent, or Firm*—Lawrence S. Levinson; Merle J. Smith; Stephen B. Davis

[57] ABSTRACT

Amino-1,2,4-oxadiazolyl-3-acetyl penicillins and cephalosporins of the general formula

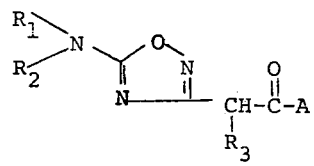

wherein A is either

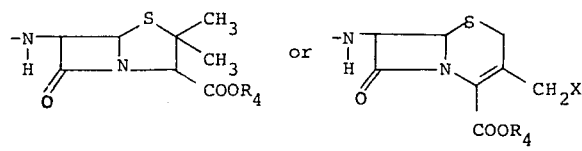

$R_1$ and $R_2$ are independently selected from hydrogen and lower alkyl or $R_1$ and $R_2$ together with the nitrogen atom to which they are attached form a heterocyclic ring; $R_3$ is hydrogen, lower alkyl, phenyl, hydroxyphenyl, thienyl, furyl, or pyridyl; $R_4$ is hydrogen, lower alkyl, phenyl-lower alkyl, benzhydryl, a salt forming ion, trimethylsilyl, or

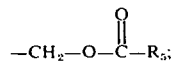

$R_5$ is lower alkyl, phenyl or phenyl-lower alkyl; X is hydrogen, lower alkoxy, lower alkanoyloxy, lower alkylmercapto, the radical of a nitrogen base; or certain heterocyclic thio moieties; are disclosed. They are useful as antibacterial agents.

5 Claims, No Drawings

AMINO-1,2,4-OXADIAZOLYL-3-ACETYL CEPHALOSPORINS

SUMMARY OF THE INVENTION

This invention relates to new amino-1,2,4-oxadiazolyl-3-acetyl penicillins and cephalosporins of the formula (I)

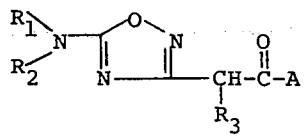

wherein A represents 6-aminopenicillanic acid (6-APA) of the formula (II)

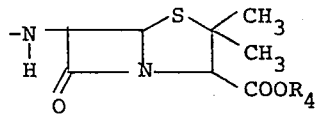

and certain derivatives thereof, or 7-aminocephalosporanic acid (7-ACA) of the formula (III)

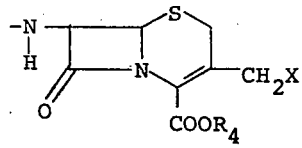

or certain derivatives thereof.

The symbols have the following meaning in formulas I, II and III and throughout this specification.

$R_1$ and $R_2$ are selected from hydrogen and lower alkyl or $R_1$ and $R_2$ taken toghether with the nitrogen atom to which they are attached form a 5- to 7-membered saturated heterocyclic radical such as 1-piperidinyl, 4-morpholinyl, 1-piperazinyl, 1-pyrrolidinyl, and the like.

$R_3$ is hydrogen, lower alkyl, phenyl, hydroxyphenyl, thienyl, furyl, or pyridyl.

$R_4$ is hydrogen, lower alkyl, phenyl-lower alkyl, benzhydryl, an inorganic or organic salt forming ion, trimethylsilyl, or the group

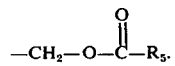

$R_5$ is lower alkyl, phenyl, or phenyl-lower alkyl.

X is hydrogen, lower alkoxy, lower alkanoyloxy, lower alkylmercapto, the radical of a nitrogen base, or heterocyclic thio moieties selected from

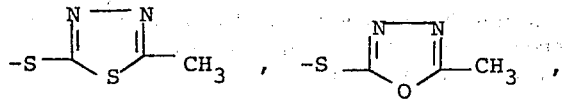

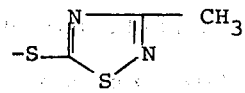

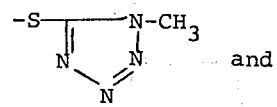 and 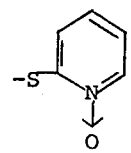

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The phenyl-lower alkyl groups include such lower alkyl groups attached to a phenyl, e.g., benzyl, phenethyl, etc.

The salt forming ions represented by $R_4$ may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine.

The radicals of a nitrogen base represented by X may be radicals of an amine, e.g., methylamine, ethylamine, dimethylamine, triethylamine, dibenzylamine, N,N'-dibenzylpyridinium, pyridinium, 1-quinolinium, 1-picolinium, etc.

The thienyl, furyl and pyridyl groups when employed as the $R_3$ substituents are attached at any available position such as 2- or 3-thienyl, 2- or 3-furyl, 2-, 3-, or 4-pyridyl.

Preferred embodiments of this invention are as follows:

$R_1$ and $R_2$ are selected from hydrogen and lower alkyl of 1 to 4 carbons or together with the nitrogen atom to which they are attached form a heterocyclic ring selected from 1-piperidinyl, 4-morpholino, 1-piperazinyl and 1-pyrrolidinyl.

$R_3$ is hydrogen, lower alkyl of 1 to 4 carbons, phenyl, hydroxyphenyl, thienyl, furyl, or pyridyl.

R₄ is hydrogen, lower alkyl of 1 to 4 carbons, benzyl, phenethyl, benzhydryl, aluminum, alkaline earth metal, alkali metal, trimethylsilyl or

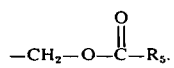

R₅ is lower alkyl of 1 to 4 carbons, phenyl, benzyl, or phenethyl.

X is hydrogen, lower alkanoyloxy of 2 to 5 carbons, lower alkoxy of 1 to 4 carbons, lower alkylmercapto of 1 to 4 carbons, pyridinium,

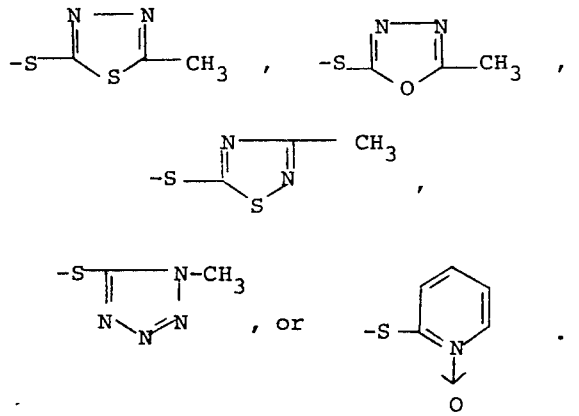

The most preferred embodiments are:

R₁ and R₂ are selected from hydrogen and lower alkyl of 1 to 4 carbons, especially hydrogen and methyl.

R₃ is hydrogen, phenyl, hydroxyphenyl, thienyl, furyl, or pyridyl, especially phenyl or 2-thienyl.

R₄ is hydrogen or benzhydryl, especially hydrogen.

X is hydrogen or lower alkanoyloxy of 2 to 5 carbons, especially

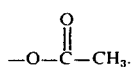

The new compounds of this invention are prepared by the acylation of a 6-aminopenicillanic acid of formula II [which includes 6-aminopenicillanic acid (6-APA) and other derivatives] or a 7-aminocephalosporanic acid of formula III [which includes -amino--aminocephalosporanic acid (7-ACA), 7-amino3-desacetoxycephalosporanic acid (7-ADCA) and other derivatives] with a reactive derivative of an acid of the formula (IV)

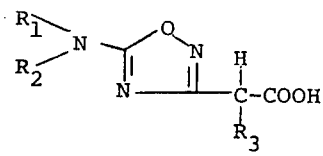

Reactive derivatives of the acid of formula IV include, for example, acid halides, acid anhydrides, mixed anhydrides of the acid of formula IV with carboxylic acid monoesters, trimethylacetic acid or benzoic acid, acid azides, active esters such as cyanomethyl ester, nitrophenyl ester or 2,4-dinitrophenyl ester, or active amides such as acylimidazoles.

The reaction of the compounds of formulas II and III with the acids of formula IV can also be effected in the presence of carbodiimides such as dicyclohexylcarbodiimide, isoxazolium salts such as N-ethyl-5-phenylisoxazolium-3′-sulfonate, or 2-ethoxy-1,2-dihydroquinoline-1-carboxylic acid ester.

The acids of formula IV can be prepared by the following methods.

A substituted acetonitrile of the formula (V)     NC—CH₂—R₃ 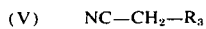

is reacted with hydroxylamine to yield an amidoxime of the formula

The amidoxime of formula VI is treated with trichloroacetyl chloride in the presence of a base such as pyridine to yield a substituted-1,2,4-oxadiazole of the formula (VII)

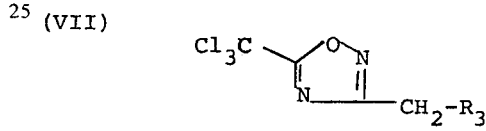

which in turn is treated with an amine of the formula

to yield the substituted-1,2,4-oxadiazole of the formula (IX)

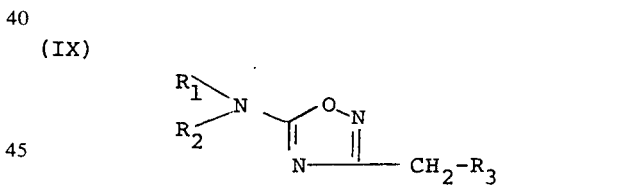

which in turn is treated with a solution of butyl lithium and a source of carbon dioxide to yield the acid of formula IV.

Alternatively, the acids of formula IV can be prepared by treating a compound of the formula

with hydroxylamine to yield a compound of the formula

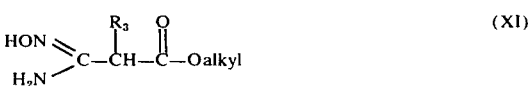

which in turn is treated with trichloroacetyl chloride in the presence of a base such as pyridine to yield a substituted-1,2,4-oxadiazole of the formula (XII)

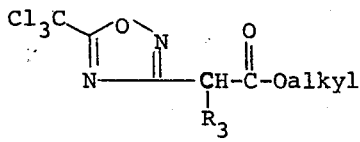

The compound of formula XII is treated with an aqueous solution of an acid such as HCl to yield the acid of formula (XIII)

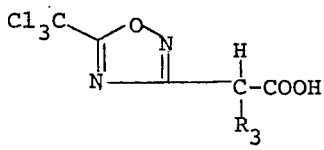

which in turn is treated with an amine of formula VIII to yield the acid of formula IV.

The preferred reactive derivatives of the acids of formula IV are the acid halides, particularly the acid chlorides which can be prepared by reacting the acid with thionyl chloride.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus, Salmonella schottmuelleri, Proteus vulgaris, Escherichia coli, Streptococcus pyogenes* and especially *Pseudomonas aeruginosa*.

They may be used as antibacterial agents in a prophylactic manner, e.g., in cleaning or disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 2.5 to 5.0 mg./kg. in mice.

Oral forms give prompt high blood levels which are maintained for relatively long periods.

Up to about 600 mg. of a compound of formula I or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.01 to 0.5% by weight of such compounds admixed with, suspended or dissolved in conventional inert dry or aqueous carriers for application by washing or spraying. They are also useful as nutritional supplements in animal feeds.

The following examples are illustrative of the invention. All temperatures are on the centigrade scale. Additional variations may be produced in the same manner by appropriate substitution in the starting material.

EXAMPLE 1

6β-[[(5-Amino-1,2,4-oxadiazol-3-yl)phenylacetyl-]amino]-3,3-dimethyl-7-oxo-4-thia-1-azabicyclo[3.2.0]heptane-2-carboxylic acid a. 5-Amino-3-(phenylmethyl)-1,2,4-oxadiazole A mixture of 60 g. (0.22 moles) of 3-(phenylmethyl)-5-trichloromethyl-1,2,4-oxadiazole and 50 ml. of ether are added dropwise with stirring into 100 ml. of liquid ammonia and stirred for an additional hour. The ammonia and ether are evaporated, the residue is treated with a little water and filtered under suction. 33.3 g. of 5-amino-3-(phenylmethyl)-1,2,4-oxadiazole are obtained, m.p. 142°–145°. After recrystallization from ethanol the compound melts at 145°–146°.

b. 5-Amino-α-phenyl-1,2,4-oxadiazole-3-acetic acid 260 g. (0.507 mole + 20%) of a 15% solution of butyl lithium in n-hexane is cooled to –60° under nitrogen. At this temperature a solution of 27.6 g. of 5-amino-3-(phenylmethyl)-1,2,4-oxadiazole in 300 ml. of absolute tetrahydrofuran is added dropwise with stirring over a period of about 2½ hours. The reaction mixture is stirred for an additional 30 minutes. Then over a period of 2 hours a proportionate stream of carbon dioxide is passed through the mixture. The cold bath is removed and the reaction mixture is permitted to come to room temperature. This mixture is concentrated in a rotary evaporator, the residue is treated with water and adjusted to pH 8. The aqueous solution is extracted with ether and the aqueous phase is acidified with 2N hydrochloric acid. The precipitate is filtered under suction and reprecipitated twice by dissolving in dilute sodium hydroxide solution and acidifying with dilute hydrochloric acid. 7.4 g. of 5-amino-α-phenyl-1,2,4-oxadiazole-3-acetic acid are obtained, m.p. 163°–164° (dec.).

c. 5-Amino-α-phenyl-1,2,4-oxadiazole-3-acetyl chloride 3.6 g. of the 5-amino-α-phenyl-1,2,4-oxadiazole-3-acetic acid obtained in part (b) are added to 60 ml. of thionyl chloride at room temperature. 0.5 ml. of dimethylformamide are added and the reaction mixture is heated for 30 minutes on a bath at 40°. The clear solution is concentrated in a rotary evaporator. The oily residue is taken up in 50 ml. of anhydrous chloroform, filtered and again concentrated. The crude 5-amino-α-phenyl-1,2,4-oxadiazole-3-acetyl chloride is used without further purification.

d. 6β-[[(5-Amino-1,2,4-oxadiazol-3-yl)phenylacetyl-]amino]-3,3-dimethyl-7-oxo-4-thia-1-azabicyclo[3.2.0]heptane-2-carboxylic acid 2.0 g. of 6-aminopenicillanic acid are brought into solution in 60 ml. of absolute chloroform at 0° by the addition of 2.7 ml. of triethylamine. The solution is stirred for 30 minutes. 1.9 g. of the crude acid chloride from part (c) dissolved in 50 ml. of absolute chloroform are added dropwise at –5° and stirred for 1 hour at 0°–5°. 30 ml. of ethyl acetate are added and the reaction mixture is acidified to pH 1 by the addition of 1N hydrochloric acid. The organic phase is separated, filtered and extracted three times with sodium bicarbonate solution. The combined aqueous solution is extracted once with ether, layered over with 50 ml. of ethyl acetate, cooled to 0° and acidified to pH 1 with 2N hydrochloric acid. The ethyl acetate phase is clarified with a little activated carbon, extracted twice with 20 ml. of sodium bicarbonate solution and the product, 6β-[[(5-amino-1,2,4-oxadiazol-3-yl)phenylacetyl]amino]-3,3-dimethyl-7-oxo-4-thia-1-azabicyclo[3.2.0]heptane-2-carboxylic acid, is precipitated from the aqueous solution with 2N hydrochloric acid, yield 0.6 g., m.p. 173°–175° (dec.).

EXAMPLE 2

3-[(Acetyloxy)methyl]-7β-[[(5-amino-1,2,4-oxadiazol-3-yl)phenylacetyl]amino]-8-oxo-5-thia-1-azabicyclo[4.2.0]oct-2-ene-2-carboxyl acid 2.55 g. of 7-aminocephalosporanic acid, brought into solution in 60 ml. of absolute chloroform with 3.4 ml. of triethylamine, are treated with the acid chloride obtained in Example 1 (c) to obtain 0.6 g. of 3-[(acetyloxy)methyl]-7β-[[(5-amino-1,2,4-oxadiazol-3-yl)phenylacetyl]amino]-8-oxo-5-thi -1-azabicyclo[4.2.0]oct-2-ene-2-carboxylic acid, m.p. 110°–115° (dec.).

EXAMPLE 3

3-[(Acetyloxy)methyl]-7β-[[(5-amino-1,2,4-oxadiazol-3-yl)-2-thienylacetyl]amino]-8-oxo-5-thia-1-azabicyclo[4.2.0]oct-2-ene-2-carboxylic acid a. 3-(2-Thienylmethyl)-5-(trichloromethyl)-1,2,4-oxadiazole 290 g. (2.35 moles) of 2-thienylacetonitrile is treated with the equivalent amount of alcoholic hydroxylamine solution and stirred overnight to obtain 2-thienylacetamidoxime. By concentrating, treating the residue with anhydrous chloroform, filtering and again concentrating, the crude amidoxime is obtained in the form of a syrup. The syrupy residue is dissolved in 1000 ml. of anhydrous dioxane and the cooled solution is treated dropwise first with 854 g. of trichloroacetyl chloride then with 380 ml. of pyridine. The mixture is then stirred overnight at room temperature. The dioxane is distilled off in a rotary evaporator and the residue is added to a liter of water. The oily substance which separates is treated with ether. The ether solution is repeatedly washed with water, neutralized with saturated sodium bicarbonate solution, washed several times with water and dried with magnesium sulfate. After concentrating, the residue is treated with 750 ml. of toluene and refluxed in a reflux condensor for about 2 hours. A small amount of water is removed. The toluene solution is treated with activated carbon, filtered, concentrated and the residue is distilled under vacuum. 258 g. of 3-(2-thienylmethyl)-5-(trichloromethyl)-1,2,4-oxadiazole are obtained, b.p. $_{0.01}$ 119°–122°.

b. 5-Amino-3-(2-thienylmethyl)-1,2,4-oxadiazole 124.8 g. (0.44 moles) of the 3-(2-thienylmethyl)-5-(trichloromethyl)-1,2,4-oxadiazole obtained in part (a) are dissolved in 100 ml. of ether and added dropwise to 200 ml. of liquid ammonia at −45° with stirring. This mixture is stirred for one more hour and then the ammonia and solvent are permitted to evaporate overnight. The solid residue is treated with water and filtered under suction. 75 g. of crude 5-amino-3-(2-thienylmethyl)-1,2,4-oxadiazole are obtained which is recrystallized from isopropanol, yield 52.5 g., m.p. 132°–133°.

c. 5-Amino-α-(2-thienylmethyl)-1,2,4-oxadiazole-3-acetic acid 86.2 g. of a 15% solution of butyl lithium in n-hexane are cooled to −60°. A solution of 10.2 g. of the 5-amino-3-(2-thienylmethyl)-1,2,4-oxadiazole obtained in part (b) are added dropwise under nitrogen. The rather viscous suspension is stirred for 15 minutes. Then a stream of carbon dioxide is passed through the suspension at −60° for 2½ hours. The mixture is stirred overnight at room temperature, evaporated to dryness and the residue is treated with water and filtered. The aqueous solution is acidified, treated with ether and the ether is evaporated to obtain the crude product. After recrystallizing several times from isopropanol and from ethyl acetate-benzene, the 5-amino-α-(2-thienylmethyl)-1,2,4-oxadiazole-3-acetic acid is obtained analytically pure in good yield, m.p. 136° (dec.).

d. 3-[(Acetyloxy)methyl]-7β-[[(5-amino-1,2,4-oxadiazol-3-yl)-2-thienylacetyl]amino]-8-oxo-5-thia-1-azabicyclo[4.2.0]-oct-2-ene-2-carboxylic acid 1.36 g. (0.005 moles) of 7-aminocephalosporanic acid, 10 ml. of absolute methylene chloride and 0.57 g. of hexamethyldisilazane are refluxed for 3 hours under nitrogen to obtain the trimethylsilyl ester of 7-aminocephalosporanic acid (solution A).

1.15 g. (0.005 moles) of the 5-amino-α-(2-thienylmethyl)-1,2,4-oxadiazole-3-acetic acid obtained in part (c) are dissolved in 10 ml. of absolute tetrahydrofuran at 0° and 1.03 g. of dicyclohexylcarbodiimide are added. After stirring for 30 minutes, solution A is added dropwise. This mixture is stirred overnight at 0°, the precipitate is filtered off under suction and the filtrate is concentrated under vacuum. The residue is treated with a small amount of ethyl acetate and 10 drops of water are added. A precipitate is removed by filtering under suction. The product, 3-[(acetyloxy)methyl]-7β-[[(5-amino-1,2,4-oxadiazol-3yl)2-thienylacetyl]amino]-8-oxo-5-thia-1-azabicyclo[4.2.0]oct-2-ene-2-carboxylic acid, is precipitated from the filtrate by the addition of petroleum ether, yeild 0.7 g.

EXAMPLE 4

3-[(Acetyloxy)methyl]-7β-[[(5-(dimethylamino)-1,2,4-oxadiazol-3-yl)phenylacetyl]amino]-8-oxo-5-thia-1-azabicyclo[4.2.0]oct-2-ene-2-carboxylic acid a. 5-(Dimethylamino)-3-(phenylmethyl)-1,2,4-oxadiazole 3-(Phenylmethyl)-5-(trichloromethyl)-1,2,4-oxadiazole is reacted with dimethylamine to yield 5-(dimethylamino)-3-(phenylmethyl)-1,2,4-oxadiazole.

b. 5-(Dimethylamino)-α-phenyl-1,2,4-oxadiazole-3-acetic acid 5-(Dimethylamino-3-(phenylmethyl)-1,2,4-oxadiazole from part (a) is treated with a solution of butyl lithium and carbon dioxide according to the procedure of Example 1 (b) to yield 5-(dimethylamino)-α-phenyl-1,2,4-oxadiazole-3-acetic acid.

c. 5-(Dimethylamino)-α-phenyl-1,2,4-oxadiazole-3-acetyl chloride 5-(Dimethylamino)-α-phenyl-1,2,4-oxadiazole-3-acetic acid from part (b) is trated with thiony chloride according to the procedure of Example 1 (c) to yield 5-(dimethylamino-α-phenyl-1,2,4-oxadiazole-3-acetyl chloride.

d. 3-[(Acetyloxy)methyl]-7β-[[(5-(dimethylamino)-1,2,4-oxadiazol-3-yl)phenylacetyl]amino]-8-oxo-5-thia-1-azabicyclo[4.2.0]oct-2-ene-2-carboxylic acid 5-(Dimethylamino)-α-phenyl-1,2,4-oxadiazole-3-acetyl chloride obtained in part (c) is treated with 7-aminocephalosporanic acid according to the procedure of Example 2 to yield 3-[(acetyloxy)methyl]-7β-

[[(5-(dimethylamino)-1,2,4-oxadiazol-3-yl)phenylacetyl]amino]-8-oxo-5-thia-1-azabicyclo[4.2.0]oct-2-ene-2-carboxylic acid.

EXAMPLE 5

3-[(Acetyloxy)methyl]-7β-[[(5-amino-1,2,4-oxadiazol-3-yl)acetyl]amino]-8-oxo-5-thia-1-azabicyclo[4.2.0]oct-2-ene-2-carboxylic acid a. 5-trichloromethyl)-1,2,4-oxadiazol-3-acetic acid, ethyl ester 417 g. of hydroxylamine hydrochloride are suspended in 600 ml. of ethanol. To the suspension is added gradually with stirring and cooling a solution of 430 g. of potassium hydroxide in 2.9 liters of ethanol until the suspension remains alkaline to phenolphthalein. The potassium chloride is filtered off under suction and to the alcoholic hydroxylamine solution obtained is added a solution of 847 g. of cyanoacetic acid ethyl ester in 1 liter of ethanol. The mixture is stirred overnight at room temperature. Then the precipitate is filtered off under suction and the filtrate is concentrated in a rotary evaporator. The residue is treated with 1 liter of dioxane and concentrated to remove the ethanol completely. This procedure is repeated once more. The residue is then treated with 3 liters of dioxane, 1217 ml. of pyridine are added and 1012 ml. of trichloracetyl chloride are added slowly dropwise with cooling and stirring. This mixture is stirred overnight, the crystals (pyridine hydrochloride) are filtered under suction, the filtrate is concentrated and 2 liters of water are added to the residue. An oil separates which is treated with ether and very thoroughly washed with water and then with sodium bicarbonate solution until the ether solution is no longer acidic. The ether is separated under vacuum. The residue is distilled under high vacuum to obtain 308 g. of 5-(trichloromethyl)-1,2,4-oxadiazole-3-acetic acid, ethyl ester, b.p. $_{0.2mm}$ 97°–103°.

b. 5-(Trichloromethyl)-1,2,4-oxadiazole-3-acetic acid 203 g. of the 5-(trichloromethyl)-1,2,4-oxadiazole-3-acetic acid, ethyl ester obtained in part (a) is heated to 80° with 2.2 liters of dioxane, 700 ml. of water and 75 ml. of concentrated hydrochloric acid for 2 hours. The solvent is evaporated under vacuum and the solid residue is filtered under suction to obtain 138 g. of 5-(trichloromethyl)-1,2,4-oxadiazole-3-acetic acid; m.p. 127°–131°. The product is recrystallized from benzene, m.p. 129°–131°.

c. 5-Amino-1,2,4-oxadiazole-3-acetic acid 12.2 g. of the 5-(trichloromethyl)-1,2,4-oxadiazole-3-acetic acid obtained in part (b) are added portionwise to 80 ml. of liquid ammonia. The substance immediately forms a clear solution. After the addition, the ammonia is permitted to evaporate and the residue is crystallized from approximately 80% alcohol. The ammonium salt of 5-amino-1,2,4-oxadiazole-3-acetic acid is obtained, m.p. 195° (dec.). The free acid is obtained by dissolving 3 g. of the ammonium salt in 6 ml. of water, cooling to 5° and acidifying with 2N hydrochloric acid. 2.25 g. of 5-amino-1,2,4-oxadiazozle-3-acetic acid precipiate, m.p. 169° (dec.).

d. 3-[(Acetyloxy)methyl]-7β-[[(5-amino-1,2,4-oxadiazol-3-yl)-acetyl]amino]-8-oxo-5-thia-1-azabicyclo[4.2.0]oct-2-ene-2-carboxylic acid 1 g. of the 5-amino-1,2,4-oxadiazole-3-acetic acid from part (c) is dissolved in 30 ml. of absolute tetrahydrofuran and 1.45 g. of dicyclohexylcarbodiimide are added. This solution is added at 0° to a solution formed from 1.52 g. of 7-aminocephalosporanic acid and 1.55 ml. of triethylamine and 30 ml. of absolute chloroform. The mixture is stirred overnight at 0°–5°. This mixture is then filtered and the filtrate is concentrated in a rotary evaporator. The residue is dissolved in 20 ml. of methanol and 2 ml. of a 2N potassium ethylhexanoate solution in n-butanol are added. A turbidity is filtered off. The potassium salt of 3-[(acetyloxy)methyl]-7β-[[(5-amino-1,2,4-oxadiazol-3-yl)acetyl]amino]-8-oxo-5-thia-1-azabicyclo[4.2.0]-oct-2-ene-2-carboxylic acid is precipitated by the addition of ether. 0.3 g. of the crude potassium salt is dissolved in a little water, filtered and acidified with 2N hydrochloric acid. The product crystallizes from the aqueous solution. 0.14 g. of 3-[(acetyloxy)methyl]-7β-[[(5-amino-1,2,4-oxadiazol-3-yl)acetyl]amino]-8-oxo-5-thia-1-azabicyclo[4.2.0]oct-2-ene-2-carboxylic acid are obtained, m.p. 158°–160° (dec.).

EXAMPLES 6–16

By substituting the amine shown in column 1 for the ammonia in Example 1 (a) one obtains the following 5-substituted-3-(phenylmethyl)-1,2,4-oxadiazole shown in column 2 which can be converted to the appropriate 6β-[[(5-substituted-1,2,4-oxadiazol-3-yl)phenylacetyl]amino]-3,3-dimethyl-7-oxo-4-thia-1-azabicyclo[3.2.0]heptane-2-carboxylic acid or 7β-[[(5-substituted-1,2,4-oxadiazol-3-yl)phenylacetyl]amino]-8-oxo-5-thia-1-azabicyclo [4.2.0]oct-2-ene-2-carboxylic acid by following the procedures of Examples 1 or 2.

| Ex. | $R_1$ | $R_2$ |
|---|---|---|
| 6 | $C_2H_5$ | $C_2H_5$ |
| 7 | $C_3H_7$ | $C_3H_7$ |
| 8 | $C_4H_9$ | $C_4H_9$ |
| 9 | H | $CH_3$ |
| 10 | $CH_3$ | $C_2H_5$ |
| 11 | $CH_3$ | $C_3H_7$ |
| 12 | H | $C_4H_9$ |

In the following Examples, 13 to 16, $R_1$ and $R_2$ taken together with the nitrogen atom to which they are attached form heterocyclic rings.

| Ex. | ring |
|---|---|
| 13 | piperidino |
| 14 | pyrrolidino |
| 15 | piperazino |
| 16 | morpholino |

EXAMPLES 17–27

Following the procedure of Example 3 but employing the appropriate substituted-acetonitrile for the 2-thienylacetonitrile in part (a) one obtains the following compounds of formula I:

| Ex. | |
|---|---|
| 17 | 3-[(Acetyloxy)methyl]-7β-[[(5-amino-1,2,4-oxadiazol-3-yl)methylacetyl]amino]-8-oxo-5-thia-1-azabicyclo[4.2.0]oct-2-ene-2-carboxylic acid |
| 18 | 3-[(Acetyloxy)methyl]-7β-[[(5-amino-1,2,4-oxadiazol-3-yl)ethylacetyl]amino]-8-oxo-5-thia-1-azabicyclo[4.2.0]oct-2-ene-2-carboxylic acid |
| 19 | 3-[(Acetyloxy)methyl]-7β-[[(5-amino-1,2,4-oxadiazol-3-yl)propylacetyl]amino]-8-oxo-5-thia-1-azabicyclo[4.2.0]oct-2-ene-2-carboxylic acid |
| 20 | 3-[(Acetyloxy)methyl]-7β-[[(5-amino-1,2,4-oxadiazol-3-yl)butylacetyl]amino]-8-oxo-5-thia-1-azabicyclo[4.2.0]oct-2-ene-2-carboxylic acid |
| 21 | 3-[(Acetyloxy)methyl]-7β-[[(5-amino-1,2,4-oxadiazol-3-yl)hydroxyphenylacetyl]amino]-8-oxo-5-thia-1-azabicyclo[4.2.0]oct-2-ene-2-carboxylic acid |
| 22 | 3-[(Acetyloxy)methyl]-7β-[[(5-amino-1,2,4-oxadiazol-3-yl)3-thienylacetyl]amino-8-oxo-5-thia-1-azabicyclo[4.2.0]oct-2-ene-2-carboxylic acid |
| 23 | 3-[(Acetyloxy)methyl]-7β-[[(5-amino-1,2,4-oxadiazol-3-yl)2-furylacetyl]amino]-8-oxo-5-thia-1-azabicyclo[4.2.0]oct-2-ene-2-carboxylic acid |
| 24 | 3-[(Acetyloxy)methyl]-7β-[[(5-amino-1,2,4-oxadiazol-3-yl)3-furylacetyl]amino]-8-oxo-5-thia-1-azabicyclo[4.2.0]oct-2-ene-2-carboxylic acid |
| 25 | 3-[(Acetyloxy)methyl]-7β-[[(5-amino-1,2,4-oxadiazol-3-yl)2-pyridylacetyl]amino]-8-oxo-5-thia-1-azabicyclo[4.2.0]oct-2-ene-2-carboxylic acid |
| 26 | 3-[(Acetyloxy)methyl]-7β-[[(5-amino-1,2,4-oxadiazol-3-yl)3-pyridylacetyl]amino]-8-oxo-5-thia-1-azabicyclo[4.2.0]oct-2-ene-2-carboxylic acid |
| 27 | 3-[(Acetyloxy)methyl]-7β-[[5-amino-1,2,4-oxadiazol-3-yl)4-pyridylacetyl]amino]-8-oxo-5-thia-1-azabicyclo[4.2.0]oct-2-ene-2-carboxylic acid |

Similarly, the penicillanic acid compounds corresponding to the cephalosporanic acid compounds of Examples 17 to 27 are obtained by substituting 6-APA for the 7-ACA.

EXAMPLES 28–48

Following the procedure of Example 1 but employing the 6-aminopenicillanic acid derivatives shown in column 1 for the 6-aminopenicillanic acid one obtains the following compounds shown in column 2:

Column 1    Column 2

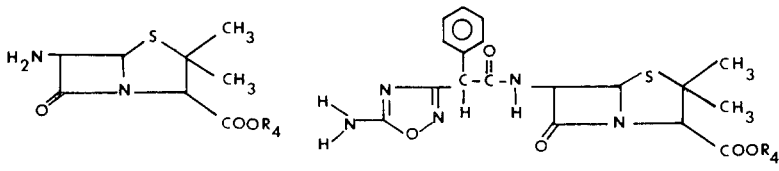

| Ex. | R₄ |
|---|---|
| 28 | $CH_3$ |
| 29 | $C_2H_5$ |
| 30 | $i\text{-}C_3H_7$ |
| 31 | $C_4H_9$ |
| 32 | $-CH_2-C_6H_5$ |
| 33 | $-CH(C_6H_5)_2$ |
| 34 | Al/3 |
| 35 | Na |
| 36 | Ca/2 |
| 37 | Mg/2 |
| 38 | K |
| 39 | $Si(CH_3)_3$ |
| 40 | $[CH_3NH_3]^+$ |
| 41 | $[(C_6H_5-CH_2)_2NH_2]^+$ |
| 42 | $-CH_2-O-C(=O)-CH_3$ |
| 43 | $-CH_2-O-C(=O)-C_2H_5$ |
| 44 | $-CH_2-O-C(=O)-C_3H_7$ |
| 45 | $-CH_2-O-C(=O)-C_4H_9$ |
| 46 | $-CH_2-O-C(=O)-C_6H_5$ |

-continued

| Column 1 | Column 2 |
|---|---|
| 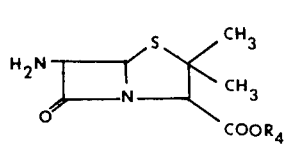 | 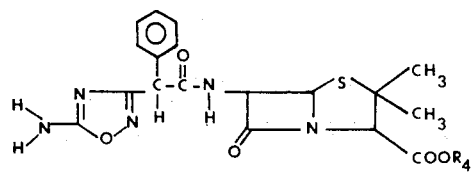 |
| 47 | 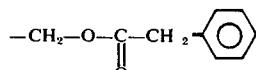 |
| 48 | 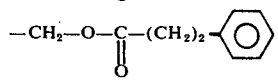 |

EXAMPLES 49–68

Following the procedure of Example 2 but employing the 7-aminocephalosporanic acid derivatives shown in column 1 for the 7-aminocephalosporanic acid one obtains the following compounds shown in column 2:

Column 1          Column 2

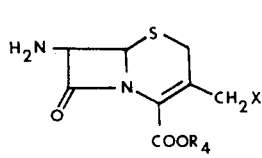          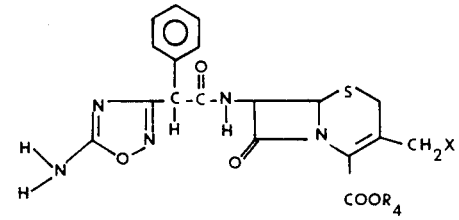

| Ex. | $R_4$ | X |
|---|---|---|
| 49 | H | H |
| 50 | $CH_3$ | H |
| 51 | $C_2H_5$ | $-OCH_3$ |
| 52 | $i-C_3H_7$ | $-OC_2H_5$ |
| 53 | $-CH_2-C_6H_5$ | H |
| 54 | $-CH_2-CH_2-C_6H_5$ | $-O-\overset{O}{\underset{\|}{C}}-CH_3$ |
| 55 | H | $-O-\overset{O}{\underset{\|}{C}}-C_2H_5$ |
| 56 | $CH_3$ | $-O-\overset{O}{\underset{\|}{C}}-C_3H_7$ |
| 57 | $-CH_2-O-\overset{O}{\underset{\|}{C}}-CH_3$ | H |
| 58 | Na | $-O-\overset{O}{\underset{\|}{C}}-CH_3$ |
| 59 | $[CH_3NH_3]^+$ | H |
| 60 | $-CH\begin{smallmatrix}C_6H_5\\C_6H_5\end{smallmatrix}$ | $-O-\overset{O}{\underset{\|}{C}}-CH_3$ |
| 61 |  | pyridinium |
| 62 | H | $-S-CH_3$ |
| 63 | H | $-S-C_3H_7$ |
| 64 | H | $-S-\underset{S}{\overset{N-N}{\diagdown\diagup}}-CH_3$ |

| Column 1 | Column 2 |
|---|---|

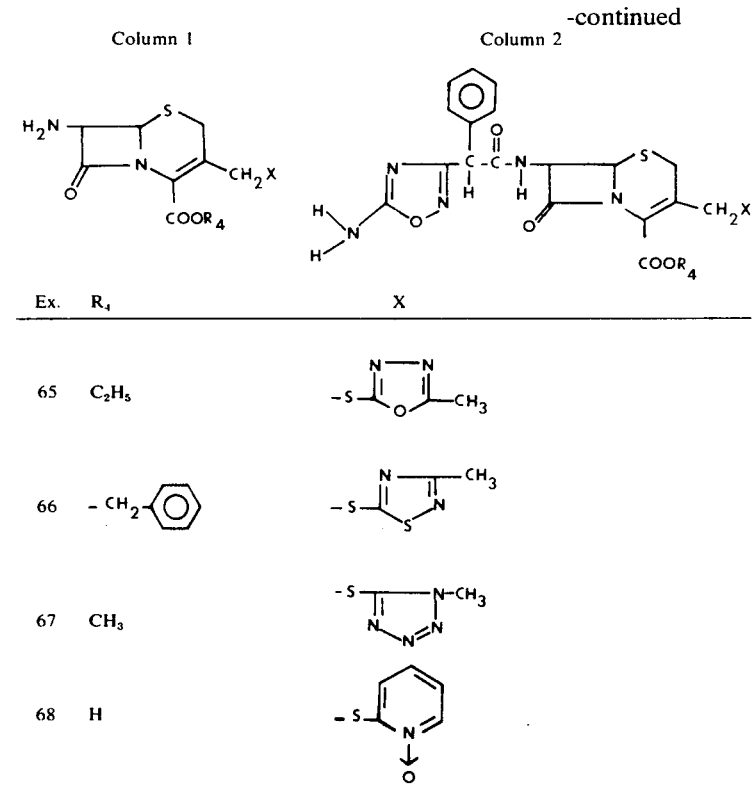

| Ex. | $R_4$ | X |
|---|---|---|
| 65 | $C_2H_5$ | -S-[1,3,4-oxadiazol-2-yl]-CH_3 |
| 66 | -CH_2-C_6H_5 | -S-[4-methylthiazol-2-yl] |
| 67 | $CH_3$ | -S-[1-methyltetrazol-5-yl] |
| 68 | H | -S-[pyridine N-oxide-2-yl] |

The 6-aminopenicillanic acid derivatives of col. 1 in Examples 28 to 48 and the 7-aminocephalosporanic acid derivatives of col. 1 in Examples 49–68 can be employed in Examples 6 to 27 to obtain compounds of formula I having the various $R_1$, $R_2$, $R_3$, $R_4$ and X substituents.

What is claimed is:

1. A compound of the formula:

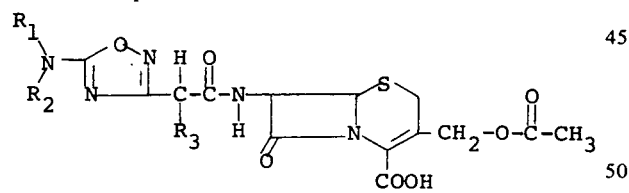

wherein $R_1$ and $R_2$ are independently selected from the group consisting of hydrogen and methyl; $R_3$ is phenyl or 2-thienyl; or a physiologically acceptable salt thereof.

2. The compound of claim 1 wherein $R_1$ and $R_2$ are both hydrogen.

3. The compound of claim 2 wherein $R_3$ is phenyl.

4. The compound of claim 2 wherein $R_3$ is 2-thienyl.

5. The compound of claim 1 wherein $R_1$ and $R_2$ are both methyl and $R_3$ is phenyl.

* * * * *

UNITED STATES PATENT AND TRADEMARK OFFICE
CERTIFICATE OF CORRECTION

PATENT NO. : 3,960,849
DATED : June 1, 1976
INVENTOR(S) : Hermann Breuer

It is certified that error appears in the above-identified patent and that said Letters Patent are hereby corrected as shown below:

Col. 3, line 48, "-amino--" should be cancelled.

Col. 3, line 49, --7-- should be inserted at the beginning of the line.

Col. 7, line 12, "carboxyl" should read --carboxylic--.

Col. 7, line 18, "thi" should read --thia--.

Col. 8, line 33, "3yl" should read --3-yl--.

Col. 9, line 15, "phenolp-" should read -- phenolph- --.

Signed and Sealed this

Seventh Day of September 1976

[SEAL]

Attest:

RUTH C. MASON
*Attesting Officer*

C. MARSHALL DANN
*Commissioner of Patents and Trademarks*